United States Patent [19]

Lester

[11] 3,997,590
[45] Dec. 14, 1976

[54] KETO-ESTERS

[75] Inventor: Michael George Lester, Edinburgh, Scotland

[73] Assignee: B.D.H. Pharmaceuticals Ltd., Edinburgh, Scotland

[22] Filed: June 28, 1973

[21] Appl. No.: 374,817

[30] Foreign Application Priority Data
July 14, 1972 United Kingdom ............ 33070/72

[52] U.S. Cl. .................. 260/470; 260/247.1 R;
260/247.2 B; 260/293.73; 260/293.75;
260/293.82; 260/293.85; 260/293.88;
260/294.8 G; 260/294.9; 260/295 R;
260/326.4; 260/332.2 A; 260/340.5;
260/340.9; 260/345.8; 260/347.2; 260/347.4;
260/465 D; 260/468 G; 260/468 H; 260/468
J; 260/468 K; 260/469; 260/471 R; 260/471
A; 260/473 A; 424/278; 424/248; 424/282;
424/283; 424/263; 424/285; 424/304;
424/267; 424/305; 424/308; 424/269;
424/309; 424/274; 424/275

[51] Int. Cl.² ........................................ C07C 69/95

[58] Field of Search .......... 260/473 A, 473 R, 470,
260/471 R, 465 D, 340.5, 471 A

[56] References Cited

FOREIGN PATENTS OR APPLICATIONS 924,256 4/1963 United Kingdom

OTHER PUBLICATIONS

Medicinal Chemistry, vol. 6, p. 211, edited by Campaigne, (1973).
Corsano et al., C.A., 50, p. 10663a (1956).
Panizzi et al., C.A., 49, p. 198g (1955).
Henecka et al., C.A., 43, p. 1013 (1949).

*Primary Examiner*—Jane S. Myers
*Attorney, Agent, or Firm*—Bacon & Thomas

[57] ABSTRACT

Cyclohexenone esters of the general formula I

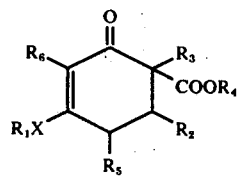

or pharmaceutically acceptable acid addition salts thereof, wherein,
X is oxygen or sulphur,
$R_1$ is
1. alkyl,
2. cycloalkyl,
3. alkenyl,
4. alkynyl,
5. aralkyl,
6. aryl,
7. pyridyl,

8.

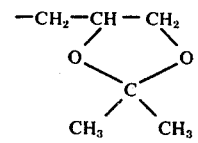

or
9. —$(CH_2)_mY$ in which Y is perhalogenoalkyl, hydroxy, hydroxyalkoxy, hydroxyalkoxyalkoxy, alkoxy, alkoxyalkoxy, acyloxy or alkoxycarbonyl, or Y is—$S(CH_2)_nOZ$, in which Z is acyl, $m$ and $n$ each represent integers of 1 to 3

$R_2$ is
1. hydrogen,
2. alkyl, optionally substituted by alkoxy or alkoxycarbonyl,
3. alkoxycarbonyl,
4. cycloalkyl,
5. cycloalkenyl,
6. aryl, aralkyl, or aralkenyl in which the aryl portion may be substituted by alkyl, alkoxy, alkoxyalkyl, methylenedioxy, alkoxycarbonyl, perhalogenoalkyl, nitro, halogen, nitrile, aryl, dialkylaminocarbonyl, amino, alkylamino, dialkyamino or aralkoxy,
7. a saturated or unsaturated heterocyclic ring containing one or more heteroatoms and which ring may be substituted by alkyl,

8.

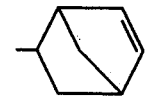

or
9.

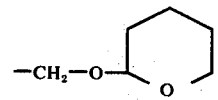

$R_3$ is
1. hydrogen,
2. alkyl, which may be substituted with alkoxycarbonyl, carboxyl, amino, alkylamino, dialkylamino, or heterocyclic,
3. alkenyl which may be substituted with alkylcarbonyl or alkoxycarbonyl,
4. alkynyl, or
5. aralkyl, $R_4$ is
1. alkyl,
2. alkoxyalkyl,
3. alkenyl, or
4. aralkyl, $R_5$ is
hydrogen, alkyl, aryl or alkoxycarbonyl, and
$R_6$ is
hydrogen, alkyl or aryl;

with the proviso that when $R_1$ and $R_4$ are ethyl, and $R_3$, $R_5$ and $R_6$ are hydrogen then $R_2$ may not be a methyl.

These compounds have biological activity, particularly as anaesthetics.

16 Claims, No Drawings

KETO-ESTERS

This invention relates to new organic chemical compounds which have biological activity, particularly on the central nervous system. More particularly many of the compounds exhibit a general anaesthetic activity.

The invention accordingly provides cyclohexenone esters of the general formula I:

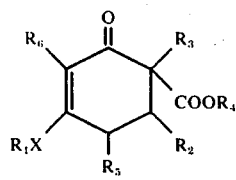

I or pharmaeutically acceptable acid addition salts thereof, wherein;

X is an oxygen or sulphur atom
$R_1$ is either
1. a straight or branched chain alkyl group,
2. a cycloalkyl group,
3. an alkenyl group,
4. an alkynyl group,
5. an aralkyl group,
6. an aryl group,
7. a pyridyl group,
8. a group of the formula

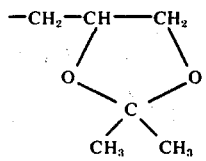

9. a group of thr formula $-(CH_2)_mY$ in which Y is either a perhalogenoalkyl, hydroxy, hydroxyalkoxy, hydroxyalkoxyalkoxy, alkoxy, alkoxyalkoxy, acyloxy or alkoxycarbonyl group or Y is a $-S-(CH_2)_nOZ$ group, in which Z is an acyl group, m and n which may be the same or different, each represent integers of 1 to 3

$R_2$ is either
1. a hydrogen atom,
2. a straight or branched chain alkyl group; optionally substituted by one or more alkoxy or alkoxycarbonyl groups,
3. an alkoxycarbonyl group,
4. a cycloalkyl group,
5. a cycloalkenyl group,
6. an aryl, aralkyl or aralkenyl group in which the aryl portion may optionally be substituted by one or more alkyl, alkoxy, alkoxyalkyl, methylenedioxy, alkoxycarbonyl, perhalogenoalkyl, nitro, halogen, nitrile, aryl, dialkylaminocarbonyl, amino, alkylamino, dialkylamino or aralkoxy groups,
7. a saturated or unsaturated heterocyclic ring containing one or more heteroatoms and which ring may be optionally substituted by alkyl,
8. a group of the formula:

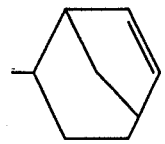

9. a group of the formula:

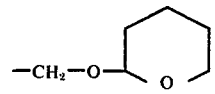

$R_3$ is either
1. a hydrogen atom,
2. a straight or branched chain alkyl group, which may be substituted with alkoxycarbonyl, carboxyl, amino, alkylamino, dialkylamino, or heterocyclic groups,
3. an alkenyl group which may be substituted with an alkylcarbonyl or alkoxycarbonyl group,
4. an alkynyl group, or
5. an aralkyl group.

$R_4$ is either
1. a straight or branched chain alkyl group,
2. an alkoxyalkyl group,
3. an alkenyl group, or
4. an aralkyl group, $R_5$ is either
a hydrogen atom, an alkyl, aryl or alkoxycarbonyl group, and $R_6$ is
a hydrogen atom, or an alkyl or aryl group;
with the proviso that when $R_1$ and $R_4$ are ethyl groups, and $R_3$, $R_5$ and $R_6$ are hydrogen atoms then $R_2$ may not be a methyl group.

Preferred meaning for the groups given above are as follows:

$R_1$ is a straight or branched chain $C_1$ to $C_9$ alkyl, more preferably $C_1$ to $C_6$ alkyl;

$R_2$ is a $C_1$ to $C_6$ straight or branched chain alkyl group or a substituted aryl group, particularly a tolyl group;

$R_3$ is a straight or branched chain $C_1$ to $C_9$ alkyl group (more preferably containing 1 to 6 carbon atoms); if the alkyl group is substituted by a heterocyclic group this is preferably a morpholino or piperidino group, but $R_3$ is most preferably a hydrogen atom, $R_4$ is a $C_1$ to $C_6$ alkyl group;
$R_5$ is a hydrogen atom, or a $C_1$ to $C_6$ alkyl group;
$R_6$ is a hydrogen atom or a $C_1$ to $C_6$ alkyl group.

When the compounds contain basic nitrogen atoms they may of course be in the form of pharmaceutically acceptable acid addition salts.

The numbering of the cyclohexenone system used herein is as follows:

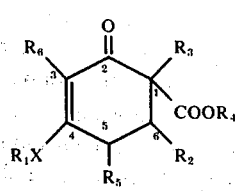

We have also found that these compounds in which X is oxygen can be prepared from compounds of formula II by reaction with an alcohol of formula $R_1OH$; the other groups in the formula II having the meanings given above. The compounds of formula II are referred to herein, for brevity, as "the diones".

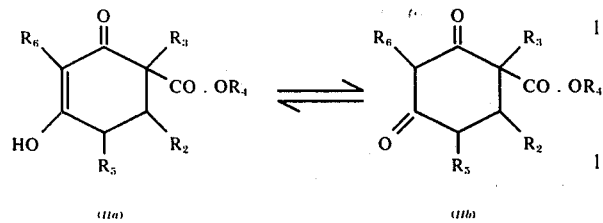

(IIa)   (IIb)

It will be appreciated that the diones of formula II may exist in various tautomeric forms and the reaction of the alcohol $R_1OH$ with compounds II to give the compounds according to the invention can be considered to be replacement of the enolic 4-OH group present in the enol form IIa by the group $OR_1$.

Accordingly compounds of the formula I, in which X is an oxygen atom can be prepared by reacting diones of formula II with an alcohol of formula $R_1OH$ in the presence of an acid, preferably of p-toluenesulphonic acid.

Alternatively compounds of formula I in which x is an oxygen atom can be prepared by reacting a metal enolate salt of formula III:

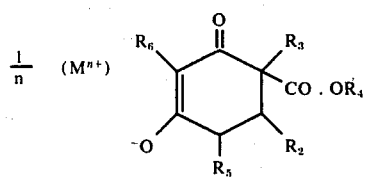

in which $R_2$ to $R_6$ are as defined above, M is a metal ion, preferably an alkali metal ion, of valency n, with a halide of formula $R_1Hal$, in which Hal is a halogen atom, preferably chlorine, bromine or iodine and $R_1$ is as defined above. The metal enolate salts III are, of course, simply the salts of the enol IIa.

It will be appreciated that there are other theoretically possible tautomers of the diones II, apart from IIa and IIb. However the ester carbonyl group in the 1 position exerts a strong directing influence on the enolisation of the carbonyl groups in the 2 and 4 positions and formation of the enol form IIa is favoured. Thus in the reactions discussed above only small amounts of the undesired isomers having a $2\text{-}OR_1$ group rather than a $4\text{-}OR_1$ group are formed.

The compounds I, in which X is a sulphur atom, can be prepared by first converting diones of formula II into the corresponding halo compounds of formula IV (in which Hal is a halogen atom preferably a chlorine, bromine or iodine atom)

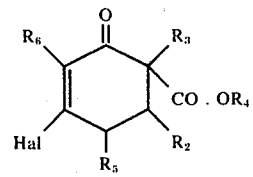

and then reacting these with salts derived from thiols of formula $R_1SH$.

The invention therefore also provides a process for the production of cyclohexenone esters of the general formula I:

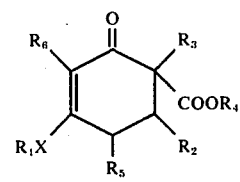

in which $R_1$ to $R_6$ and X are as defined above, which comprises a dione of the general formula II:

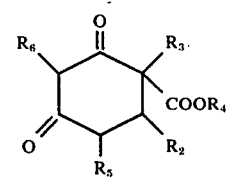

or a tautomer thereof, with an alcohol of formula $R_1OH$ in the presence of acid, to give a cyclohexenone ester of formula I in which X is an oxygen atom; or (b) reacting a metal enolate salt of formula III (in which M is a metal ion of valency $n$):

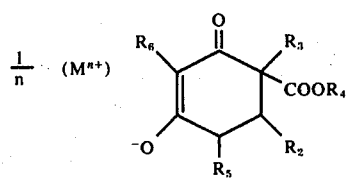

with a halide of formula $R_1Hal$, in which Hal is a halogen atom to give a cyclohexenone ester of formula I in which X is an oxygen atom; or (c) reacting a halide of formula IV:

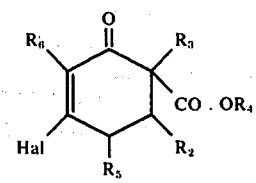

in which Hal is a halogen atom with a salt of a thiol of formula $R_1SH$ to give a cyclohexenone ester of formula I in which X is a sulphur atom; if desired in all cases with subsequent conversion of one or more of the groups $R_1$ to $R_6$ to other groups within the meaning given.

The conversion of the diones II to the metal enolate salts can be carried out by treatment with a suitable base under anhydrous conditions; preferably with a metal hydride, e.g. NaH. The following equation illustrates this reaction:

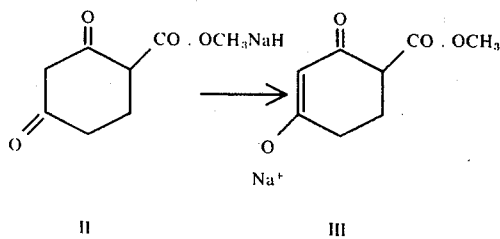

Quite frequently when the diones II are being prepared they are initially obtained in the form of the metal enolate salt III which may then be converted to the parent dione II. However, if desired, the metal enolate salt III may be reacted directly with the halide $R_1Hal$ to give the compound I. This method avoids the need for preparing the dione II itself. However, generally speaking, it is preferred to isolate the dione II and then to react this with the alcohol $R_1OH$ in the presence of acid.

The halo compounds IV can be prepared from the diones II with a suitable anhydrous halogenating agent e.g. thionyl chloride, $PCl_3$, $PCl_5$, $PBr_5$ or $POCl_3$. We prefer to make the chloro compounds using phosphorus oxychloride in an inert polar solvent, e.g. dimethylformamide.

The halo compounds IV can be reacted with the salts of the thiols $R_1SH$ in similar inert polar solvents, e.g. dimethyl sulphoxide or dimethylformamide. The thiols $R_1SH$ are converted into salts by treatment with base, preferably with a metal hydride, e.g. sodium hydride.

The diones of formula II may be prepared by Michael type additions of active methylene compounds (preferably malonate or acetoacetate esters) to $\alpha,\beta$-unsaturated esters or ketones followed by cyclisation.

FIG. 1 indicates the way in which amalonate diester will condense with an $\alpha,\beta$-unsaturated ketone to give the diones of formula II. FIG. 2 illustrates the way in which a $\beta$-keto ester will condense with a $\alpha,\beta$-unsaturated ester to give the compounds of formula II. In both these figures the R groups have the meanings given above for the compounds according to the invention. The groups $R_8$, which are eliminated during the reaction, are preferably alkyl groups and in the case where malonate diesters are used $R_8$ is often identical to $R_9$. $R_9$ is preferably an alkyl group and is usually the same as $R_4$.

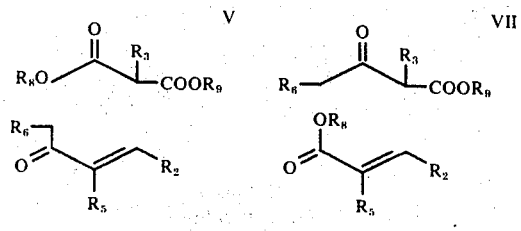

Thus according to the invention the diones of formula II may have been prepared by condensation, in the presence of base (preferably an alkali metal alkoxide) of a malonate diester of the formula V given in FIG. 1 with an $\alpha,\beta$-unsaturated ketone of formula VI given in FIG. 1, wherein the groups $R_2 - R_6$ are as defined above, $R_8$ is an alkyl group and $R_9$ is the same as $R_4$ or is an alkyl group. It is particularly preferred to use diethyl malonate as the compound V. This process is referred to herein as the malonate route.

The invention also provides a further process for the production of the diones of formula II wherein a $\beta$-keto ester of formula VII, as given in FIG. 2, is condensed in the presence of base (preferably an alkali metal alkoxide) with an $\alpha,\beta$-unsaturated ester of formula VIII as given in FIG. 2, wherein the groups $R_2 - R_6$ are as defined above, $R_8$ is an alkyl group and $R_9$ is the same as $R_4$ or is an alkyl group. It is particularly preferred to use ethyl acetoacetate as the compound VII. This process is referred to herein as the acetoacetate route.

Once a compound of formula I has been prepared one can, if desired, replace one $R_4$ group by another by transesterification.

Furthermore a compound of formula I in which $R_3$ is a hydrogen atom can be converted into other compounds of formula I in which $R_3$ is some other group. This is because the carbon atom at position 1 is activated both by the ester carbonyl and the carbonyl group at position 2 and can therefore be alkylated, as can dialkyl malonate or alkyl acetoacetate. Thus when $R_3$ is not a hydrogen atom there are two general synthetic approaches. In the first the $R_3$ group is substituted into the malonic or acetoacetic ester by an alkylation type reaction before this is condensed with the $\alpha,\beta$-unsaturated ketone or ester.

These alkylation type reactions are well known in the art and usually involve treating the malonic or acetoacetic ester with base (e.g. sodium hydride or potassium tert-butoxide) followed by reaction with an alkyl halide or other halide of formula $R_3Hal$. In the second method, which is generally preferred, the compound I having $R_3 = H$ is prepared and only then is the $R_3$ group substituted for the hydrogen atom by a similar base-catalysed alkylation type reaction.

This reaction is preferably carried out in solution in a highly polar anhydrous solvent, e.g. dimethylformamide or dimethyl sulphoxide, at temperatures between room temperature and about 60° C. The base used is preferably sodium hydride. After the base has reacted with the cyclohexenone compound the compound $R_3Hal$ (preferably $R_3Br$ or $R_3I$) is added and this reacts to give the cyclohexeone ester of formula I having the new $R_3$ group.

The compounds according to the invention tend to have a depressant effect on the central nervous system and many have anaesthetic activity whilst some may have analgesic activity. It has been found that many compounds are of particular value as induction anaesthetics. These are quick acting anaesthetics, given by injection, in order to produce rapid anaesthesia and to allow the convenient administration of other general anaesthetics.

The compounds may be formulated, for example, as tablets, pills, dragees, suppositories, ointments or lotions with pharmaceutically acceptable carriers and/or adjuvants. When they are to be used as induction anaesthetics they are preferably formulated in liquid form suitable for intravenous or intramuscular injection, e.g. as aqueous solutions or suspensions. When used as induction anaesthetics a dosage of 0.5 to 200 mg/kg, preferably 0.5 to 50 mg/kg, and most preferably 1 to 10 mg/kg is suitable. The invention accordingly provides such pharmaceutical formulations, in particular in a form suitable for injection, if desired packages in dosage units, containing the whole or a part of the desired dose.

Some of the compounds according to the invention are not easily water soluble and, when using these to produce injectable aqueous solutions, they are preferably formulated using surface active agents which will solubilise the compounds according to the invention. A pharmaceutically acceptable surface active agent which can be used for this purpose is Cremophor EL, which is a polyoxyethylated castor oil.

The compounds according to the invention are rendered more water soluble if they contain a polar or salt group in one of the substituents. Thus, we have found, for example, that when $R_2$ is a p-dimethylaminophenyl group this will form salts which have water solubility.

Tests carried out by intravenous administration of the compounds to mice have shown that many have desirable general anaesthetic properties, as determined by the loss of the righting reflex. From these tests it appears that, in mice, the advantageous effects of altering the substituents $R_3$, $R_5$ and $R_6$ are not very marked. Hence it is generally preferred that these groups be hydrogen atoms. The substituents $R_1$ and $R_4$ appear to be more important but, generally speaking it is preferred that these be lower alkyl ($C_{1-6}$) groups. It appears that the value of $R_2$ has a most important effect on the anaesthetic activity of the compounds and we have found that these compounds in which $R_2$ is a tolyl group are particularly potent. Hence in a preferred class of compounds the groups $R_3$, $R_5$ and $R_6$ are hydrogen atoms, $R_1$ is a lower alkyl group containing 1 to 6 carbon atoms (preferably ethyl or methyl) and $R_4$ is a lower alkyl group containing 1 to 6 carbon atoms (preferably methyl or ethyl). $R_2$ is preferably a substituted aromatic group, particularly a substituted phenyl group. $R_2$ is most preferably a tolyl group, in which the methyl group is preferably in the para position. Thus the compound of Example 1 has been found to have an anaesthetic activity better than thiopentone.

The invention is further illustrated by the following Examples which detail many of the new compounds and describe the preparation of a number of the new compounds:

EXAMPLE 1 (acetoacetate route)

Ethyl 4-ethoxy-2-oxo-6-p-tolyl-3-cyclohexenecarboxylate

To a cooled solution of sodium ethoxide (from 2.3 g. sodium and 30 ml. absolute ethanol) was added with shaking ethyl acetoacetate (13 g.). When homogeneous the mixture was treated with ethyl p-methylcinnamate (19 g.) and then heated under reflux for 18 hrs. After cooling the crystalline precipitate was collected by filtration and washed with acetone. Dissolution in cold water followed by acidification with 2N-hydrochloric acid afforded crystalline ethyl 2,4-dioxo-6-p-tolylcyclohexanecarboxylate (a dione of formula II).

Treatment of the latter compound (5g) in dry ethanol (50 ml.) with p-toluenesulphonic acid (0.5 g.) at 20° C for 3 hrs. followed by pouring the mixture into 10 volumes of water containig $Na_2CO_3$ (2g.) and ether extraction gave, after evaporation of the ether, 4.5 g. crude product. Crystallisation from ether/light petroleum afforded ethyl 4-ethoxy-2-oxo-6-p-tolyl-3-cyclohexenecarboxylate m.p 75°-7° C.

EXAMPLE 2

Ethyl 2-oxo-4n-propoxy-6-p-tolyl-3-cyclohexenecarboxylate

Ethyl 2,4-dioxo-6-p-tolycyclohexanecarboxylate (5g.) prepared as in Example 1, dissolved in n-propanol (75 ml.) was treated with p-toluenesulphonic acid (0.5 g.) and the mixture was cooled to 0° C and kept at that temperature for 24 hrs. Pouring the mixture into excess aqueous $Na_2CO_3$ solution followed by ether extraction afforded the crude product (4.9 g.) which when crystallised from ether/hexane afforded ethyl 2-oxo-4-n-propoxy-6-p-tolyl-3-cyclohexenecarboxylate m.p. 106°-7° C.

EXAMPLE 3

Ethyl 4-($\beta$-ethoxyethoxy)-2-oxo-6-p-tolyl-3-cyclohexenecarboxylate

A mixture of ethyl 2,4-dioxo-6-p-tolylcyclohexanecarboxylate (5 g.) prepared as in Example 1, and p-toluenesulphonic acid (0.5 g.) dissolved in 2-ethoxyethanol (50 ml.) was allowed to stand at 25° C for 16 hrs. Pouring the mixture into excess aqueous $Na_2CO_3$ solution followed by ether extraction afforded a mauve coloured solution containing the product. After decolourisation of the solution with activated charcoal, evaporation of solvents and crystallisation of the residue from ether/cyclohexane afforded ethyl 4-ethoxyethoxy-2-oxo-6-p-tolyl-3cyclohexenecarboxylate m.p. 59°-60° C.

EXAMPLE 4

Ethyl 4-isopropoxy-2-oxo-6-p-tolyl-3-cyclohexenecarboxylate

This compound was prepared from 2,4-dioxo-6-p-tolylcyclohexanecarboxylate and isopropanol by the method of Example 2. Crystallisation from ether/hexane afforded ethyl 4-iso-propoxy-2-oxo-6-p-tolyl 3-cyclohexenecarboxylate, m.p. 108°-9° C.

EXAMPLE 5 (acetoacetate route)

Methyl 4-ethoxy-2-oxo-6-p-tolyl-3-cyclohexenecarboxylate

To a cooled solution of sodium methoxide (from 2.3 g., sodium and absolute methanol, 40 ml.) was added with shaking methyl acetoacetate (11.8 g.). When homogeneous the mixture was treated with ethyl p-methylcinnamate (19. g.) and then heated under reflux for 18 hrs. After cooling the precipitated sodium enolate salt (formula III) was collected by filtration and washed with acetone. This enolate salt was then converted to the corresponding dione of formula II by dissolving in cold water followed by acidification with 2-N-hydrochloric acid, which afforded crystalline methyl 2,4-dioxo-6-p-tolylcyclohexanecarboxylate.

The latter compound was treated with p-toluenesulphonic acid and dry ethanol as described in Example 1. Crystallisation of the product from ether/light pertroleum afforded methyl 4-ethoxy-2-oxo-6-p-tolyl-3-cyclohexenecarboxylate m.p. 124°-7° C.

EXAMPLE 6 (malonate route)

Ethyl 6-(p-dimethylaminophenyl) 4-ethoxy-2-oxo-3-cyclohexenecarboxylate

To a solution of sodium ethoxide (from 2.3 g. sodium and dry ethanol 35 ml.) was added slowly diethyl malonate (14 g.). After the addition the mixture was heated under reflux for 1 minute, cooled and then treated with 4-p-dimethylaminophenyl-3-buten-2-one (14.5 g.). After heating under reflux for 17 hrs. the mixture was cooled and the precipitated sodium enolate salt (formula III) was collected by filtration, washed with acetone and then dissolved in cold water. Conversion to the corresponding dione II was carried out by gradually acidifying the solution with 2N-hydrochloric acid until further addition of acid caused no further precipitation. The precipitated material was collected by filtration, washed with water and dried to afford ethyl 6-p-dimethylaminophenyl-2,4-dioxocyclohexanecarboxylate.

Treatment of the latter compound (4.52 g.) in dry ethanol (50 ml.) with p-toluene sulphonic acid (4.3 g.) at 25° C for 3 hrs. followed by pouring the mixture into excess aqueous $Na_2CO_3$ solution and ether extraction gave, after evaporation of the solvent, 4.1 g. crude product. Preparative chromatography on 20 × 40 cm $SiO_2$ plates using multiple development with a mixture of cyclohexane and ethyl acetate (2:1 by volume) followed by elution with ether afforded ethyl 6-p-dimethylaminophenyl-4-ethoxy-2-oxo-3-cyclohexenecarboxylate m.p. 64° C (ether/light petroleum).

EXAMPLE 7 (malonate route)

Ethyl 4-ethoxy-6-(2-furyl)-2-oxo-3-cyclohexenecarboxylate

To a solution of sodium ethoxide (from 2.3 g. sodium and dry ethanol 35 ml.) was added slowly diethyl malonate (14 g.). After the addition the mixture was heated under reflux for 1 minute, cooled and then treated with 4-(2-furyl)-3-buten -2-one (13 g.). After heating under reflux for 17 hrs. and cooling, the precipitated sodium enolate salt (of formula III) was collected by filtration, washed with acetone and dissolved in water. The solution was acidified with 2N-sulphuric acid (to convert the enolate salt to the corresponding dione II) and extracted with dichloromethane. After washing the organic layer with water and drying over sodium sulphate, removal of solvents under reduced pressure afforded ethyl 2,4-dioxo-6-(2-furyl)-cyclohexanecarboxylate.

Treatment of the latter compound with dry ethanol and p-toluenesulphonic acid by the method described in Example 6, and preparative chromatography gave ethyl 4-ethoxy-6-(2-furyl)-2-oxo-3-cyclohexenecarboxylate as a viscous oil (λmax 250 nm : ε 16,700)

EXAMPLE 8 (acetoacetate route)

Ethyl 2-oxo-6-phenyl-4-(2-propynyloxy)-3-cyclohexenecarboxylate

To a cooled solution of sodium ethoxide (from 2.3 g. sodium and absolute ethanol, 30 ml.) was added with shaking ethyl acetoacetate (13 g.). When homogeneous the mixture was treated with ethyl cinnamate (17.8 g.) and then heated under reflux for 18 hrs. After cooling the solution, the precipitated enolate salt (formula III) was collected by filtration and washed with acetone. Dissolution in cold water, followed by acidification with 2N-sulphuric acid (to convert the enolate salt to the corresponding dione II) afforded crystalline ethyl 2,4-dioxo-6-phenylcyclohexanecarboxylate.

Treatment of the latter compound (5 g.) in propargyl alcohol (75 ml.) with p-toluenesulphonic acid (0.5 g.) at 0° C for 16 hrs. followed by pouring the mixture into excess aqueous $Na_2CO_3$ solution and ether extraction gave, after evaporation of solvent, 5 g. crude product. This was chromatographed on 20 × 40 cm $SiO_2$ plates (2 mm thickness) at a plate loading of 0.5 g. and development with a mixture of toluene and ethyl acetate (5:1 by volume). Elution of the major component with ether afforded, after evaporation of the solvents, ethyl 2-oxo-6-phenyl-4-(2-propynyloxy)-3-cyclohexenecarboxylate, m.p. 86°–7° C (dichloromethane/light petroleum).

EXAMPLE 9 (acetoacetate route)

Ethyl 4-ethoxy-6-m-methoxyphenyl-2-oxo-3-cyclohexenecarboxylate

To a cooled solution of sodium ethoxide (from 2.3 g. sodium and absolute ethanol, 30 ml.) was added with shaking, ethyl acetoacetate (13 g.). When homogeneous the mixture was treated with ethyl m-methoxycinnamate (20.6 g.) and then heated under reflux for 18 hrs. After cooling the crystalline precipitate of the enolate salt (formula III) was collected by filtration and washed with acetone. Dissolution in water followed by acidification with $2N-H_2SO_4$ afforded ethyl, 2,4-dioxo-6 -m-methoxyphenylcyclohexanecarboxylate, which is the corresponding dione II.

Treatment of the latter compound with dry ethanol and p-toluenesulphonic acid by the method described in Example 6 followed by preparative chromatography afforded ethyl 4-ethoxy-6-m-methoxyphenyl-2-oxo-3-cyclohexenecarboxylate as a viscous oil, (λ max 251.5 nm: ε 16,640).

EXAMPLE 10 (acetoacetate route)

Ethyl 6-(3-cyclohexenyl)-4-ethoxy-1-methyl-2-oxo-3-cyclohexenecarboxylate

To a cooled solution of sodium ethoxide (from 2.3 g. sodium and absolute ethanol, 30 ml.) was added with shaking ethyl 2-methylacetoacetate (14.2 g.). When homogeneous the mixture was treated with ethyl 3-(cyclohexenyl)acrylate (16.8 g.) and then heated under reflux for 18 hrs. After cooling the mixture was diluted with 500 ml. water and extracted with ether and the extracts discarded. The aqueous solution was then acidified with 2N-hydrochloric acid and extracted with ether. After washing the ether solution with water and drying over $Na_2SO_4$, evaporation of the solution afforded ethyl 6-(3-cyclohexenyl)-2,4-dioxo-1-methylcyclohexanecarboxylate.

The latter compound was treated with p-toluenesulphonic acid and dry ethanol by the method given in Example 6. Preparative chromatography gave ethyl 6-(3-cyclohexenyl) 4-ethoxy-1-methyl-2-oxo-3-cyclohexenecarboxylate as a viscous oil, (λmax 253 nm:ε15,550).

EXAMPLE 11 (acetoacetate route)

Ethyl 4-ethoxy-2-oxo-5-phenyl-3-cyclohexenecarboxylate

To a cooled solution of sodium ethoxide (from 2.3 g. sodium and dry ethanol, 30 ml.) was added with shaking ethyl acetoacetate (13 g.). When homogeneous the mixture was treated with ethyl atropate (17.7g.) and then heated under reflux for 16 hrs. After cooling the mixture was diluted with 500 ml. water and ether extracted. The ether extracts were discarded. Acidification of the aqueous portion with 2N-HCl followed by ether extraction gave after evaporation of solvents a dione of formula II, viz- ethyl 2,4,dioxo-5-phenylcyclohexanecarboxylate.

The latter compound (5 g.) and p-toluenesulphonic acid (0.5 g.) was dissolved in a mixture of dry EtOH (50 ml.) and benzene (300 ml.) and heated under reflux with azeotropic removal of water for 24 hrs. After cooling the mixture was shaken with excess aqueous $Na_2CO_3$ solution, washed with water, dried over $Na_2SO_4$ and the solvents removed by distillation under reduced pressure. The residual crude product weighed 4.2 g. Purification by chromatographing twice on 20 × 40 cm $SiO_2$ plates, developing with a mixture of toluene and ethyl acetate (2:1 by volume) and eluting the desired component with ether afforded ethyl 4-ethoxy-2-oxo-5-phenyl-3-cyclohexenecarboxylate as a viscous oil, ($\lambda$max 251 nm:$\epsilon$16,180).

EXAMPLE 12 (malonate route)

Ethyl 4-ethoxy-5-methyl-2-oxo-6-phenyl-3-cyclohexenecarboxylate

To a solution of sodium ethoxide (from 2.3 g. sodium and dry ethanol, 35 ml.) was added dropwise diethylmalonate (14 g.). After the addition the mixture was heated under reflux for 1 minute before cooling and adding 3-methyl-4-phenyl-3-buten-2-one (14 g). The mixture was heated under reflux for 16 hrs., cooled and the precipitated sodium enolate salt (formula III) was collected by filtration, washed with acetone and then dissolved in water. The solution was acidified with 2N-HCl and extracted with ether. After washing the organic extract with water, and drying over $Na_2SO_4$, removal of solvents under reduced pressure afforded the corresponding dione II, i.e. ethyl 2,4-dioxo-5-methyl-6-phenylcyclohexanecarboxylate.

Treatment of the latter compound with dry ethanol and p-toluenesulphonic acid by the method given in Example 1 afforded crystalline ethyl 4-ethoxy- 5-methyl-2-oxo-6-phenyl-3-cyclohexenecarboxylate, m.p. 58° C. (ether/light petroleum).

EXAMPLE 13 (malonate route)

Ethyl 4-ethoxy-2-oxo-6-o-tolyl-3-cyclohexenecarboxylate

To a solution of sodium ethoxide (from 1.9 g.sodium and dry ethanol, 30 ml.) was added dropwise diethyl malonate (13 g.). After the addition the mixture was heated under reflux for 1 minute, cooled and then treated with 4-o-tolyl-3-buten-2-one. (13 g.). After heating under reflux for 17 hrs. the mixture was cooled and the precipitated sodium enolate salt (formula III) was collected by filtration, washed with acetone and then dissolved in cold water. The solution was acidified with 2N-$H_2SO_4$ and extracted with dichloromethane. After washing the organic solution with water and drying over $Na_2SO_4$, removal of solvents under reduced pressure afforded the corresponding dione II, i.e. ethyl 2,4-dioxo-6-o-tolylcyclohexanecarboxylate.

Treatment of the latter compound with dry ethanol and p-toluenesulphonic acid by the method given in Example 1 give a crystalline product (ether/light petroleum) which was ethyl 4-ethoxy-2-oxo-6-o-tolyl-3-cyclohexenecarboxylate m.p. 101°–3° C.

EXAMPLE 14 (malonate route)

Ethyl 4-ethoxy-2-oxo-6-(4-pyridyl)-3-cyclohenecarboxylate

To a solution of sodium ethoxide (from 1.9 g. sodium and dry ethanol 30 ml.) was added dropwise diethyl malonate (13 g.). After the addition the mixture was heated under reflux for 1 minute, cooled and then treated with 4-(4-pyridyl)-3-buten-2-one (12.5 g.) After heating under reflux for 16 hrs. the mixture was cooled and the precipitated sodium enolate salt (formula III) was collected by filtration, washed with acetone and dissolved in water. Gradual acidification with 2N-HCl until no further material was precipitated followed by collection of the solid by filtration under reduced pressure and washing with water afforded the corresponding dione of formula II, viz ethyl 2,4,dioxo-6-(4-pyridyl) cyclohexanecarboxylate.

Treatment of the latter compound with dry ethanol and p-toluenesulphonic acid by the method given in Example 1 gave a crystalline product (ether/light petroleum) which was ethyl 4-ethoxy-2-oxo-6-(4-pyridyl)-3-cyclohexenecarboxylate m.p. 95°–6° C.

EXAMPLE 15 (reaction of an enolate salt with an alkyl halide)

Ethyl 4-ethoxy-2-oxo-6-p-tolyl-3-cyclohexenecarboxylate

A mixture of the sodium salt of ethyl 2,4-dioxo-6-p-tolylcyclohexanecarboxylate (of formula III from Example 1) (5 g.) and ethyl iodide (5 g.) in dimethylformamide (50 ml.) and ethanol (50 ml.) was stirred at 20° – 25° C for 16 hrs. The mixture was then diluted with 10 volumes of water and extracted with ether. After washing the ethereal solution with water and drying over sodium sulphate, evaporation of the solvents afforded a crude product which was chromatographed on 20 × 40 cm $SiO_2$ plates, development being with a mixture of cyclohexane and ethyl acetate (2:1 by volume). Elution of the desired component with ether afforded ethyl 4-ethoxy-2-oxo-6-p-tolyl-3-cyclohexenecarboxylate m.p. 75° – 7° C (ether/light petroleum).

EXAMPLE 16 (Conversion of a dione II to a halide IV and reaction with a salt of ethane thiol)

Ethyl 4-ethylthio-2-oxo-6-p-tolyl-3-cyclohexenecarboxylate

To a mixture of phosphoryl chloride (3.53 g.) and dimethylformamide (1.68 g.) at 0° C was added a cooled solution of ethyl 2,4-dioxo-6-p-tolylcyclohexanecarboxylate (6.2 g.) a dione of formula II prepared as in Example 1, in dichloromethane (60 ml.). After keeping at 0° C for 30 minutes the mixture was poured into excess 2N-$Na_2CO_3$ solution and extracted with ether. After washing the ether extracts with water and drying over magnesium sulphate, evaporation of the solvents gave crude ethyl 4-chloro-2-oxo-6-p-tolyl-3-cyclohexenecarboxylate (a halide of formula IV) as a pale yellow oil.

Without purification the latter compound (6.2 g.) dissolved in dimethylsulphoxide (30 ml.) was added gradually at room temperature under an atmosphere of nitrogen to the sodium salt of ethane thiol [prepared from ethane thiol (1.32 g.) and sodium hydride (60% dispersion in oil; 0.85 g.) in dimethyl sulphoxide (20 ml.)]. The mixture was stirred at 20° C for 1 hr. and then poured into excess 2N-sodium hydroxide solution. After extraction with ether and washing the extracts with water, evaporation of the solvents gave the product as a yellow solid. Recrystallisation from ether afforded white crystals of ethyl 4-ethylthio-2-oxo-6-p-tolyl-3-cyclohexenecarboxylate, m.p. 102° C.

EXAMPLE 17 (introduction of an $R_3$ group into a cyclohexenone ester of formula I)

Ethyl 1-(2-dimethylaminoethyl)-4-ethoxy-2-oxo-6-phenyl-3-cyclohexenecarboxylate

A 50% dispersion in oil of sodium hydride (2 g.) was freed of oil by stirring under nitrogen with light petroleum (25 ml.) followed by careful decantation of the liquid and repeating the process a second time. The residual sludge of sodium hydride was dried completely by further stirring under nitrogen until powdery, after which dry dimethylformamide (10 ml.) was added. To this suspension under nitrogen was added gradually over 0.5 hr. a solution of a cyclohexenone ester of formula I viz. ethyl 4-ethoxy-2-oxo-6-phenyl-3-cyclohexenecarboxylate m.p. 54° – 55° ( 5. 8g.)(example 38, Table 1) in dry dimethylformamide (25 ml.). After the addition the mixture was heated to 50° and kept between 50° and 60° whilst over 1 hr. N,N-dimethyl-2-chloroethylamine hydrochloride (2.9 g.) was added in portions. Finally the mixture was kept at 50° – 60° for a further 2 hrs. and then allowed to cool and stand at room temperature overnight. The product was isolated by diluting the mixture with water and extracting with ether. The ether solution was then quickly extracted with 0.5 N-hydrochloric acid (100 ml.) and the acidic extract was immediately made alkaline with sodium carbonate solution. The resulting mixture was extracted twice with ether and the combined extracts were dried over sodium sulphate and evaporated under reduced pressure affording the crude product which was chromatographed on 20 × 40 cm $SiO_2$ plates, development being with a mixture of cyclohexane and diethylamine (4 : 1 by volume). Elution of the desired component with acetone afforded another cyclohexenone ester of formula I viz. ethyl 1-(2-dimethylaminoethyl)-4-ethoxy-2-oxo-6-phenyl-3-cyclohexenecarboxylate λ max 255 nm, ε 15,470 which is also tabulated below as Example 94.

The following tables summarise the various compounds of formula I which have been prepared.

Where possible the melting point of the compound is given; if this is not available the ultra violet absorption maximum λ max is given in nm and the extinction coefficient ε.

The tables also indicate briefly the method of preparation of the dione; M inidicate the malonate route and A the acetoacetate route:

Table 1

General formula

| Example No. | $R_2$ | Route to Dione | U.V. Spectrum or m.p. λ max | ε |
|---|---|---|---|---|
| 18 | H | M | (m.p. 85–86° C) | |
| 19 | $C_2H_5$ | A | 250 | 17,100 |
| 20 | iso-$C_3H_7$ | A | 250.5 | 16,600 |
| 21 | n-$C_3H_7$ | A | 250.5 | 16,870 |
| 22 | n-$C_4H_9$ | A | 250 | 16,830 |
| 23 | n-$C_6H_{13}$ | A | 250.5 | 16,750 |
| 24 | cyclohexyl | A | 250.5 | 16,270 |
| 25 | cyclohex-3-enyl | A | 251.5 | 15,850 |
| 26 | cyclopentyl | A | 252 | 15,970 |
| 27 | —$CH(CH_3)CH_2CH_2CH_3$ | A | 250.5 | 16,080 |
| 28 | —CH(O—)(O—) (dioxolane) | A | 250.5 | 16,100 |
| 29 | —$CH(OCH_3)_2$ | A | 250.5 | 16,610 |
| 30 | —$CH(OC_2H_5)_2$ | A | 250.5 | 16,580 |
| 31* | —$CH_2$—O—(tetrahydropyranyl) | A | 251.5 | 17,360 |
| 32 | —$(CH_2)_6COOC_2H_5$ | A | 250.5 | 16,450 |
| 33 | —$COOC_2H_5$ | A | 250.5 | 15,300 |
| 34 | —$CH_2C_6H_5$ | A | (m.p. 75–76° C) | |
| 35 | —$CH(CH_3)C_6H_5$ | A | (m.p. 83–84° C) | |
| 36 | —$(CH_2)_2C_6H_5$ | M | 250.5 | 16,640 |
| 37 | —CH=CH—$C_6H_5$ | M | (m.p. 93–94° C) | |
| 38 | —$C_6H_5$ | A | (m.p. 54–55° C) | |
| 39 | 5 methyl-thienyl | M | (m.p. 54–6° C) | |
| 40 | m-tolyl | M | 251 | 16,430 |
| 41 | p-methoxymethylphenyl | A | (m.p. 67–9° C) | |
| 42 | 4-methoxyphenyl | A | (m.p. 65° C) | |

Table 1-continued

General formula: cyclohexenone with CO.OC₂H₅, C₂H₅O, and R₂ substituents

| Example No. | R₂ | Route to Dione. | U.V. Spectrum or m.p. λ max | ε |
|---|---|---|---|---|
| 43 | p-diethylaminophenyl | M | 256.5 | 29,240 |
| 44 | 2-methoxyphenyl | A | (m.p. 92–94° C) | |
| 45 | 3,4-dimethoxyphenyl | M | (m.p. 99–101° C) | |
| 46 | 3,4,5-trimethoxyphenyl | A | (m.p. 102–103° C) | |
| 47 | 4-nitrophenyl | M | (m.p. 131–132° C) | |
| 48 | m-trifluromethylphenyl | M | 251 | 16,500 |
| 49 | 3,4-methylenedioxyphenyl | A | (m.p. 87–88° C) | |
| 50 | 4-ethoxycarbonylphenyl | M | (m.p. 107–109° C) | |
| 51 | 2-(N-methylpyrrolidyl) | M | (m.p. 106–8° C) | |
| 52 | 2-thienyl | M | 245 | 19,460 |
| 53 | 2-pyridyl | M | (m.p. 49–50° C) | |
| 54 | 4-chlorophenyl | A | (m.p. 80–81° C) | |
| 55 | 4-phenylphenyl | A | (m.p. 152–154° C) | |
| 56 | 3-methyl-2-pyridyl | M | (m.p. 71° C) | |
| 57 | N,N-diethylaminocarbonylphenyl | M | (m.p. 115–116° C) | |
| 58 | 3-ethoxyphenyl | M | (m.p. 109–111° C) | |
| 59 | 5-methyl-2-furyl | M | 250 | 17,050 |
| 60 | 4-benzyloxyphenyl | M | (m.p. 79° C) | |
| 61 | 4-cyanophenyl | M | (m.p. 142–4° C) | |
| 62 | cyclopropyl | A | 250.5 | 16,800 |
| 63 | 4-ethylphenyl | M | (m.p. 68° C) | |

*Prepared from the sodium enolate salt and alkyl halide.

Table 2

General Formula: cyclohexenone with CO.OC₂H₅, R₃, C₂H₅O, and R₂ substituents

| Example No. | R₂ | R₃* | Route to Dione. | U.V. Spectrum or m.p. λ max | ε |
|---|---|---|---|---|---|
| 64 | methyl | methyl | A | 253.5 nm | 16,120 |
| 65 | methyl | ethyl | A | 253.5 | 16,370 |
| 66 | methyl | —CH₂COOC₂H₅ | A | 254 | 15,900 |
| 67 | methyl | —CH₂C≡CH | A | 254.5 | 16,410 |
| 68 | methyl | benzyl | A | 256 | 15,930 |
| 69 | methyl | n-C₇H₁₅ | A | 254 | 16,660 |
| 70 | methyl | n-C₈H₁₇ | A | 254 | 16,600 |
| 71 | methyl | —CH₂CH=CH—CO—C₅H₁₁ | A | 254 / 225 (inflex) | 18,420 / 11,650 |
| 72 | methyl | —CH₂COOH | A | (m.p. 106–108° C) | |
| 73 | methyl | n-C₃H₇ | A | 253.5 | 16,150 |
| 74 | methyl | iso-C₃H₇ | A | 251.5 | 15,290 |
| 75 | methyl | —(CH₂)₆COOC₂H₅ | A | 252 | 12,510 |
| 76 | ethyl | methyl | A | 252.5 | 15,000 |
| 77 | ethyl | ethyl | A | 253 | 16,280 |
| 78 | ethyl | —CH₂COOC₂H₅ | A | 253.5 | 16,470 |
| 79 | n-C₃H₇ | methyl | A | 252.5 | 16,060 |
| 80 | n-C₃H₇ | ethyl | A | 253 | 16,500 |
| 81 | n-C₄H₉ | methyl | A | 252.5 | 16,190 |
| 82 | n-C₆H₁₃ | methyl | A | 252.5 | 16,200 |
| 83 | cyclohexyl | methyl | A | 253 | 15,710 |
| 84 | cyclopropyl | methyl | A | 253 | 15,610 |
| 85 | cyclopentyl | methyl | A | (m.p. 78–80° C) | |
| 86 | phenyl | methyl | A | 255 | 15,490 |
| 87 | phenyl | ethyl | A | 255 | 11,480 |
| 88 | phenyl | —CH₂COOC₂H₅ | A | 254.5 | 15,640 |
| 89 | phenyl | —CH₂C≡CH | A | 255.5 | 15,900 |
| 90 | phenyl | benzyl | A | 257.5 | 15,640 |
| 91 | phenyl | —CH₂CH=CH—CO—C₅H₁₁ | A | 257 | 17,520 |
| 92 | phenyl | —CH₂COOH | A | 255 | 15,140 |
| 93 | phenyl | —CH₂CH=CH—CO.OC₂H₅ | A | 256 | 16,200 |
| 94 | phenyl | —CH₂CH₂N(CH₃)₂ | A | 255 | 15,470 |
| 95 | p-tolyl | methyl | A | 254.5 | 15,510 |
| 96 | p-tolyl | isopropyl | A | 254 | 15,100 |
| 97 | 3,4,5-trimethoxy- | | | | |

Table 2-continued

General Formula: cyclohexenone with C₂H₅O at position 4, R₂ at position 5, R₃ and CO·OC₂H₅ at position 6, ketone at position 1

| Example No. | R₂ | R₃* | Route to Dione | U.V. Spectrum λ max | ε or m.p. |
|---|---|---|---|---|---|
| 98 | phenyl | methyl | A | (m.p. 141–142° C) | |
| 99 | 2-furyl | methyl | A | 253 | 14,800 |
| 100 | (bicyclic structure) | H | A | 253 | 15,200 |
|  | (bicyclic structure) | Me | A | 252.5 | 15,150 |

*R₃ introduced after cyclisation.
*R₃ when not a hydrogen atom introduced after cyclisation.

Table 3

General Formula: cyclohexenone with R₁O at position 4, R₂ at position 5, R₃ and CO·OC₂H₅ at position 6, ketone at position 1

| Example No. | R₁ | R₂ | R₃* | Route To Dione | U.V. Spectrum λ max | or m.p. ε |
|---|---|---|---|---|---|---|
| 101 | —(CH₂)₂CH(C₂H₅)C₄H₉ | H | H | M | 251 | 15,700 |
| 102 | CH₃ | CH₃ | H | A | 249 | 16,850 |
| 103 | n-C₃H₇ | CH₃ | H | A | 269.5 | 17,100 |
| 104 | —CH₂CH=CH₂ | CH₃ | H | A | 267.5 | 15,020 |
| 105 | —CH₂COOC₂H₅ | CH₃ | H | A | 247.5 | 12,790 |
| 106 | cyclopentyl | CH₃ | H | A | 253.5 | 16,100 |
| 107 | —CH₂CCl₃ | CH₃ | H | A | 244 | 16,930 |
| 108 | phenyl | CH₃ | H | A | 251 | 15,800 |
| 109 | benzyl | CH₃ | H | A | 250.5 | 19,940 |
| 110 | —CH₂C≡CH | CH₃ | CH₃ | A | 250 | 15,140 |
| 111 | CH₃ | n-C₃H₇ | H | A | 249 | 16,220 |
| 112 | CH₃ | n-C₃H₇ | CH₃ | A | 251.5 | 15,560 |
| 113 | CH₃ | n-C₃H₇ | C₂H₅ | A | (m.p. 56–58° C) | |
| 114 | —CH₂C≡CH | C₂H₅ | H | A | 247.5 | 15,900 |
| 115 | —CH₂CF₃ | phenyl | H | A | 244 | 14,720 |
| 116 | —(CH₂)₂OH | p-tolyl | H | A | 250.5 | 16,740 |
| 117 | —CH₂C≡CH | phenyl | CH₃ | A | (m.p. 90–91° C) | |
| 118 | —CH₂C≡CH | phenyl | C₂H₅ | A | 252 | 14,230 |
| 119 | phenyl | phenyl | H | A | 252 | 19,800 |
| 120 | benzyl | phenyl | H | A | 251 | 18,850 |
| 121 | methyl | p-tolyl | H | A | (m.p. 86° C) | |
| 122 | —(CH₂)₂OAC | p-tolyl | H | A | 251 | 16,000 |
| 123 | —(CH₂)₂OCOEt | p-tolyl | H | A | 249 | 16,212 |
| 124 | —CH₂C≡CH | p-tolyl | H | A | 247.5 | 15,580 |
| 125 | —CH₂CF₃ | " | H | A | 242.5 | 14,580 |
| 126 | —CH₂OC₂H₅ | " | H | A | 250 | 17,300 |
| 127 | —(CH₂)₂OCOPh | " | H | A | 245 | 19,420 |
| 128 | —(CH₂)₂O(CH₂)₂OEt | " | H | A | 250.5 | 17,000 |
| 129 | —(CH₂)₂—O—(CH₂)₂OH | " | H | A | 250.5 | 16,720 |
| 130 | —(CH₂)₂S—(CH₂)₂OAc | " | H | A | 250 | 16,360 |
| 131 | —(CH₂)₂OC₄H₉(n) | " | H | A | 251 | 15,500 |
| 132 | —(CH₂)₂O(CH₂)₂O(CH₂)₂OH | " | H | A | 250 | 16,800 |
| 133 | —(CH₂)₃OEt | " | H | A | 253 | 14,700 |
| 134 | —(CH₂)₂O(CH₂)₂OMe | " | H | A | 250.5 | 16,000 |
| 135 | —CH₂—CH—CH₂ with O-C(Me)(Me)-O dioxolane | " | H | A | 249.5 | 16,200 |
| 136 | 3-pyridyl | " | H | A | 249 | 16,200 |
| 137 | —nC₄H₉ | " | H | A | (m.p. 70–72° C) | |
| 138 | —(CH₂)₂OMe | " | H | A | (m.p. 118° C) | |
| 139 | —CH(Me)Et | " | H | A | (m.p. 89–91° C) | |
| 140 | —CH₂CHMe₂ | " | H | A | (m.p. 116–8° C) | |

Table 3-continued

General Formula: cyclohexenone with $R_1O$-, $R_2$, $R_3$, and $-CO.OC_2H_5$ substituents

| Example No. | $R_1$ | $R_2$ | $R_3$* | Route To Dione | U.V. Spectrum or m.p. λ max  ε |
|---|---|---|---|---|---|
| 141 | $-n-C_5H_{11}$ | '' | H | A | 252    17,150 |
| 142 | $-CH_2CO_2Me$ | '' | Me | A | 253    14,850 |

*$R_3$ when not a hydrogen atom introduced after cyclisation.

Table 4

General Formula: cyclohexenone with $R_1O$-, $R_2$, and $-CO.OR_4$ substituents

| Example No. | $R_1$ | $R_2$ | $R_4$ | Route To Dione | U.V. Spectrum or m.p. λmax  ε |
|---|---|---|---|---|---|
| 143 | $CH_3$ | $CH_3$ | $CH_3$ | A | 249    16,610 |
| 144 | $C_2H_5$ | $CH_3$ | $CH_3$ | A | (m.p. 75–76° C) |
| 145 | $C_2H_5$ | $CH_3$ | $n-C_3H_7$ | A | 250.5  17,340 |
| 146 | $C_2H_5$ | $CH_3$ | $t-C_4H_9$ | A | (m.p. 91° C) |
| | | -CH(O-O) (dioxolane) | | | |
| 147 | $C_2H_5$ | phenyl | $CH_3$ | A | 251    16,800 |
| 148 | $CH_3$ | p-tolyl | $n-C_3H_7$ | A | 249    16,550 |
| 149 | $C_2H_5$ | p-tolyl | $n-C_3H_7$ | A | 251    17,150 |
| 150 | $C_2H_5$ | 4-methoxyphenyl | $CH_3$ | A | (m.p. 96–97° C) |
| 151 | $C_2H_5$ | p-tolyl | benzyl | A | (m.p. 72–3°) |
| 152 | $C_2H_5$ | p-tolyl | allyl | A | (m.p. 61–2°) |
| 153 | $-C_2H_5$ | p-tolyl | $-CH_2CH_2OEt$ | A | 251    16,100 |
| 154 | $-C_3H_7(n)$ | (p)-tolyl | $-CH(Me)_2$ | A | 250.5  16,490 |
| 155 | $-C_2H_5$ | & '' | $CH(Me)_2$ | A | 250.5  15,850 |
| 156 | $-C_3H_7(n)$ | & 4(N,N-dimethyl aminophenyl) | $C_2H_5$ | A | (m.p. 85–6° C) |

Table 5

General Formula: cyclohexenone with $C_2H_5O$-, $R_2$, $R_3$, $R_5$, $R_6$ and $-CO.OC_2H_5$ substituents

| No. | $R_2$ | $R_3$ | $R_5$ | $R_6$ | Route To Dione | U.V. Spectrum or m.p. λmax  ε |
|---|---|---|---|---|---|---|
| 157 | phenyl | H | $COOC_2H_5$ | H | A | (m.p. 107–110° C) |
| 158 | phenyl | H | H | phenyl | M | (m.p. 132–133° C) |
| 159 | $CH_3$ | H | H | $C_2H_5$ | A | 268.5  15,430 |

Table 6

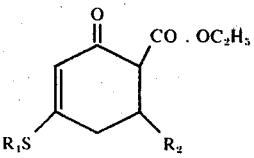

| Example No. | $R_1$ | $R_2$ | m.p. |
|---|---|---|---|
| 160 | $C_2H_5$ | phenyl | m.p 69–70°C |

In the tables the following abbreviations have been used: $Me = CH_3$; $Et = C_2H_5$; $Ac = CO.CH_3$ and $Ph = C_6H_5$ In the tables the following abbreviations have been used: $Me = CH_3$; $Et = C_2H_5$; $Ac = CO.CH_3$ and $Ph = C_6H_5$

I claim:
1. A cyclohexenone ester of the formula:

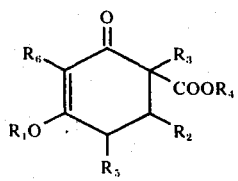

or a pharmaceutically acceptable acid addition salt thereof, wherein, $R_1$ is either
1. a straight or branched chain $C_1$ to $C_9$ alkyl group,
2. a cyclopentyl group,
3. an allyl group,
4. a propynyl group,
5. a benzyl group,
6. a phenyl group, or
7. a group of the formula $-(CH_2)_mY$ in which Y is either a $C(F)_3$, $C(Cl)_3$, hydroxy, hydroxyethoxy, hydroxyethoxyethoxy, $C_1$ to $C_4$ alkoxy, $C_1$ to $C_2$ alkoxyethoxy, acetoxy, propionyloxy, benzoyloxy or $C_1$ to $C_2$ alkoxycarbonyl group or Y is a $-S-(CH_2)_nOZ$ group, in which Z is an acetyl group, m and n which may be the same or different, each represent integers of 1 to 3;

$R_2$ is a phenyl, phenyl ($C_1$ to $C_2$) alkyl or styryl group or such a group in which the phenyl portion is substituted by at least one $C_1$ to $C_2$ alkyl, $C_1$ to $C_2$ alkoxy, methoxymethyl, methylenedioxy, ethoxycarbonyl, trifluoromethyl, nitro, halogen, nitrile, phenyl, diethylaminocarbonyl, amino, di ($C_1$ to $C_2$) alkylamino or benzyloxy group;

$R_3$ is either
1. a hydrogen atom,
2. a straight or branched chain $C_1$ to $C_9$ alkyl group or such a group substituted with an ethoxycarbonyl, carboxyl, or dimethylamino group,
3. an allyl group substituted with a hexanoyl or an ethoxycarbonyl group,
4. a propynyl group, or
5. a benzyl group;

$R_4$ is either
1. a straight or branched chain $C_1$ to $C_6$ alkyl group,
2. an ethoxyalkyl group,
3. an allyl group, or
4. a benzyl group;

$R_5$ is either a hydrogen atom, a $C_1$ to $C_6$ alkyl, phenyl or ethoxycarbonyl group; and $R_6$ is a hydrogen atom, or a $C_1$ to $C_6$ alkyl or phenyl group.

2. An ester as claimed in claim 1 in which $R_1$ is a $C_1$ to $C_6$ straight or branched chain alkyl group.

3. An ester as claimed in claim 1 in which $R_2$ is a tolyl group.

4. An ester as claimed in claim 1 in which $R_3$ is a hydrogen atom.

5. An ester as claimed in claim 1 in which $R_5$ is a hydrogen atom.

6. An ester as claimed in claim 1 in which $R_6$ is a hydrogen atom.

7. An ester as claimed in claim 1 which $R_4$ is a $C_1$ to $C_6$ alkyl group.

8. The ester of claim 1 which is ethyl 4-ethoxy-2-oxo-6-p-tolyl-3-cyclohexenecarboxylate.

9. The ester of claim 1 which is ethyl 2-oxo-4-n-propoxy-6-p-tolyl-3-cyclohexenecarboxylate.

10. The ester of claim 1 which is ethyl 4-($\beta$-ethoxyethoxy)-2-oxo-6-p-tolyl-3-cyclohexenecarboxylate.

11. The ester of claim 1 which is ethyl 4-isopropoxy-2-oxo-6-p-tolyl-3-cyclohexenecarboxylate.

12. The ester of claim 1 which is methyl 4-ethoxy-2-oxo-6-p-tolyl-3-cyclohexenecarboxylate.

13. The ester of claim 1 which is ethyl 2-oxo-6-phenyl-4-(2-propynyloxy)-3-cyclohexenecarboxylate.

14. The ester of claim 1 which is ethyl 4-ethoxy-6-m-methoxyphenyl-2-oxo-3-cyclohexenecarboxylate.

15. The ester of claim 1 which is ethyl 1-(2-dimethylaminoethyl)-4-ethoxy-2-oxo-6-phenyl-3-cyclohexenecarboxylate.

16. The ester of claim 1 which is ethyl 4-[2-(2'-acetoxyethylthio)ethoxy]-2-oxo-6-p-tolyl-3-cyclohexenecarboxylate.

* * * * *